US005925683A

United States Patent [19]

Park

[11] Patent Number: 5,925,683

[45] Date of Patent: Jul. 20, 1999

[54] LIQUID EMBOLIC AGENTS

[75] Inventor: Sangsoo Park, Kyungki-Do, Rep. of Korea

[73] Assignee: Target Therapeutics, Inc., Fremont, Calif.

[21] Appl. No.: 08/734,442

[22] Filed: Oct. 17, 1996

[51] Int. Cl.$^{6}$ .................... A61K 47/00

[52] U.S. Cl. .................... 514/772.1; 514/772.2

[58] Field of Search .................... 514/772.2, 772.1

[56] References Cited

U.S. PATENT DOCUMENTS

| | | |
|---|---|---|
| 2,160,503 | 2/1939 | Herrmann . |
| 2,657,201 | 10/1953 | Nebel . |
| 3,701,771 | 10/1972 | Almen et al. . |
| 4,364,921 | 12/1982 | Speck et al. . |
| 4,631,188 | 12/1986 | Stoy et al. . |
| 5,416,223 | 5/1995 | Klaveness et al. . |
| 5,443,454 | 8/1995 | Tanabe et al. . |
| 5,702,361 | 12/1997 | Evans et al. . |

FOREIGN PATENT DOCUMENTS

| | | |
|---|---|---|
| 0 470 569 | 2/1992 | European Pat. Off. . |
| WO 96/04954 | 2/1996 | WIPO . |

OTHER PUBLICATIONS

Novak, "Embolization materials" *Interventional Radiology* (1990) Dandlinger et al., ed., Thieme, NY, pp. 295–313.

Vinters et al., "The histotoxocity of cyanoacrylates: A selective review", *Neuroradiology* (1985) 27:279–291.

Sugawara et al., "Experimental investigations concerning a new liquid embolization method: Combined administration of ethanol–estrogen and polyvinyl acetate" *Neurol. Med. Chir.* (1993) 33:71–76.

Taki et al., "A new liquid material for embolization of arteriovenous malformations" *AJNR* (1990) 11:163–168.

Mandai et al., "Direct thrombosis of aneurysms with cellulose acetate polymer. Part I: Results of thrombosis in experimental aneurysms" *J. Neurosurg.* (1992) 77:497–500.

Takahashi et al., "Nonsurgical treatment of AVM: Development of new liquid embolization method" *Advances in Surgery for Cerebral Stroke* (1988) Suzuki, J., ed., Springer–Verlag. pp. 215–224.

Su et al., "Histopathological studies of a new liquid embolization method using estrogen–alcohol and polyvinyl acetate" *Surg. Neurol.* (1991) 36:4–11.

Janik et al., "Therapeutic embolization of the venous vascular bed with vilan 500 in animal experiments" *Cs. Radiol.* (1990) 44(1):44–50. (Translation from Czech to English by Quest Technology, Inc.).

Peregrin et al., "New material for therapeutic embolization in an animal experiment" *Cs. Radiol.* (1983) 37(1):27–33. (Translation from Czech to English by Quest Technology, Inc.).

Sugawara et al., "Experimental investigations concerning a new liquid embolization method: Combined administration of ethanol–estrogen and polyvinyl acetate" *Neurol. Med. Chir. (Tokyo)* (1993) 33:71–76.

Peregrin et al., "New occlusive agent for therapeutic embolization tested in dogs" *Cardiovasc. Intervent. Radiol.* (1984) 7(2):97–101.

Sadato et al., "Experimental study and clinical use of poly(vinyl acetate) emulsion as liquid embolisation material" *Neuradiol.* (1994) 36:634–641.

Lüscher, P. and Wintermantel, E., *A New Injectable Open–porous Implant System* (Information Brochure) ETH Zürich, Wagistr. 23, 8952 Schlieren, Switzerland, 15 pages total.

Kinugasa et al., "Direct thrombosis of aneurysms with cellulose acetate polymer Part II. Preliminary clinical experience" *J. Neurosurg.* (1992) 77:501–507.

Kinugasa et al., "Cellulose acetate polymer thrombosis for the emergency treatment of aneurysms: Angiographic findings, clinical experience, and histopathological study" *Neurosurgery* (1994) 34:694–701.

Noro, "Hydrolysis of polyvinyl acetate to polyvinyl alcohol" *Polyvinyl Alcohol* (1973) John Wiley & Sons, pp. 91–118.

Mizoi et al., "Surgical excision of giant cerebellar hemispheric arteriovenous malformations following preoperative embolization" *J. Neurosurg.* (1992) 76:1008–1011.

Akopyan et al., "Hydrolysis of polyvinylacetate" *Zhurnal Prikladnol Khimii* (1963) 336:1085–1090.

Medline Abstract 90263204. Janik et al.

*Primary Examiner*—Zohreh Fay
*Attorney, Agent, or Firm*—Morrison & Foerster

[57] ABSTRACT

This relates to a composition of matter comprising partially hydrolyzed polyvinyl acetate solutions suitable for use as embolic agent precursors. In addition, a procedure for introducing the solutions into the human body to form precipitated embolic occlusion masses is shown. Finally, a procedure for treatment of hepatic tumors using portal vein embolism is described.

48 Claims, No Drawings

LIQUID EMBOLIC AGENTS

FIELD OF THE INVENTION

This invention relates to a composition of matter comprising partially hydrolyzed polyvinyl acetate solutions suitable for use as embolic agent precursors. In addition, the invention includes a procedure for introducing the inventive solutions into the human body to form precipitated embolic occlusion masses. Finally, the invention includes a procedure for treatment of hepatic tumors using portal vein embolism.

BACKGROUND OF THE INVENTION

This invention relates to liquid polymeric compositions, or occludant precursors, that may be injected via a catheter to form occlusions in a selected body region. In particular, the compositions may be used to block blood flow in malfunctioning human organs such as the kidney, spleen, and liver, or to block blood flow into the malfunctioning areas of blood vessels such as arterio-venous malformations (AVM) and aneurysms.

The artificial blocking of blood flow is known generically as "embolization." The embolization of a vessel in an organ may be used to treat a variety of maladies; typically, though, embolization is used: 1) to control the bleeding caused by trauma, 2) to prevent profuse blood loss during an operation requiring dissection of blood vessels, 3) to obliterate a portion of or a whole organ having a tumor, or 4) to block the blood flow into abnormal blood vessel structures such as AVM's and aneurysms.

There are a variety of materials and devices which have been used for embolization. These include platinum and stainless steel microcoils, polyvinyl alcohol sponges (Ivalone), and cyanoacrylate glues (n-butyl and iso-butyl cyanoacrylate glue). See, *Interventional Radiology,* Dandlinger et al, ed., Thieme, N.Y., 1990:295–313. Of these, the cyanoacrylate glues have an advantage over other embolic materials in ease of delivery in that they are the only liquid embolics currently available to neurosurgeons. However, the constituent cyanoacrylate polymers have the disadvantage of being biodegradable. The degradation product, formaldehyde, is highly toxic to the neighboring tissues. See, Vinters et al, "The histotoxocity of cyanoacrylate: a selective review", *Neuroradiology* 1985; 27:279–291. Another disadvantage of cyanoacrylate materials is that the polymer will adhere both to the blood vessel and to the tip of the catheter. Thus physicians must retract the catheter immediately after injection of the cyanoacrylate embolic material or risk adhesion of the cyanoacrylate and the catheter to the vessel.

Another class of liquid embolic materials—precipitative materials—was invented in late 80's. See, Sugawara et al, "Experimental investigations concerning a new liquid embolization method: Combined administration of ethanol-estrogen and polyvinyl acetate", *Neuro Med Chir* (*Tokyo*) 1993; 33:71–76; Taki et al, "A new liquid material for embolization of arterio-venous malformations", AJNR 1990:11:163–168; Mandai et al, "Direct Thrombosis of aneurysms with cellulose acetate polymer. Part I: Results of thrombosis in experimental aneurysms." *J. Neurosurgery* 1992; 77:497–500. These materials employ a different mechanism in forming synthetic emboli than do the cyanoacrylate glues. Cyanoacrylate glues are monomeric and rapidly polymerize upon contact with blood. Precipitative materials, on the other hand, are pre-polymerized chains that precipitate into an aggregate upon contact with blood.

In the precipitation method, the polymer is dissolved in a solvent that is miscible with blood, and upon contact with that blood, the solvent is diluted and the water-insoluble polymer precipitates. Ideally, the precipitate forms a solid mass and thus occludes the vessel.

The first such precipitative material used in this way was polyvinyl acetate (PVAc). Takahashi et al. dissolved the polymer in an ethanol/water mixture and delivered the mixture to an AVM for embolization. Also, poly(ethylene-co-vinyl alcohol) ("EVAL") and cellulose acetate (CA) dissolved in 100% DMSO have also been used in clinical procedures. See, Taki et al, "A new liquid material for embolization of arterovenous malformations", *AJNR* 1990; 11:163–168 and Mandai et al, "Direct thrombosis of aneurysms with cellulose polymer: Part I: Results of thrombosis in experimental aneurysms", *J. Neurosurgery* 1992; 77:497–500.

One potential problem in using the precipitating polymers mentioned above is the use of organic solvents to dissolve the polymers, i.e., ethanol for PVAc and DMSO for EVAL and CA. These materials are strong organic solvents that can dissolve the catheter hub, and, in the case of DMSO, can damage microcapillary vessels and surrounding tissues. These solvents are also known to cause vasospasm of blood vessels. Although PVAc is soluble in solvents which are milder than those needed for dissolution of EVAL or CA, a PVAc solution has a problem of its own: its radio-opacity is very low, i.e., the contrast concentration is only 100 mg I/ml equivalent.

None of the cited references utilize the solvents and precipitating polymer described herein nor do they use milder organic solvents that are still insoluble in blood. The prior art compositions are not suitable for dissolving high levels of contrast medium.

SUMMARY OF THE INVENTION

As noted above, this invention involves a polymeric mixture or occlusive precursor comprising partially hydrolyzed polyvinylacetate in an aqueous organic solution. The polymeric mixture precipitates on contact with water or water-containing liquids such as blood. Preferably, the solvent is ethanol because dilute ethanol has only minor toxic or harmful effects to the human body when compared to other organic solvents.

The present invention further includes a polymeric composition containing an x-ray contrast agent. Preferably, the composition contains as much x-ray contrast agent as possible so that the injection of the inventive composition to the selected site in the body through a long catheter is visible under x-ray fluorometry and thus the injection is controllable.

In addition, the invention includes a procedure for introducing both the inventive and related solutions into the human body to form precipitated embolic occlusion masses. Finally, the invention includes a procedure for treatment of hepatic tumors using portal vein embolism.

DETAILED DESCRIPTION OF THE INVENTION

This invention is a composition of matter which may be considered an occlusive agent precursor. It is to be used to occlude selected sites within the body. Specifically, the composition comprises a mixture or solution of a.) partially hydrolyzed polyvinylacetate (PVAc) and b.) a pharmaceutically acceptable carrier solvent. The carrier solvent is selected so that it dissolves the partially hydrolyzed PVAc polymer, is acceptable for introduction into the human body with a minimum of side effects, and upon contact with blood or other body fluids precipitates from solution to form occlusive aggregates of the polymer. The inventive composition may also contain a dissolved or suspended radio-opacifier.

Generalized methods for introducing this inventive composition and related compositions into the human body also form an aspect of this invention. In particular, this invention may be used in a procedure involving portal vein embolization of portions of the liver vasculature to treat, e.g., liver tumors.

Several variables which appear to control the overall efficacy of the precursor solution as an embolizing agent include:

1.) the ratio of hydrolyzed PVAc to PVAc in the precursor solution, 2) the MW of the partially hydrolyzed PVAc, and 3) the concentration of hydrolyzed PVAc and PVAc in the carrier solvent.

Also affecting the efficacy of the use of the inventive composition is the type and concentration of radio-opacifiers used in the composition.

Partially Hydrolyzed PVAc Polymers

PVAc is a polymer whose backbone chain is hydrophobic but the side chain, the acetate group, is moderately hydrophilic. The hydrophilicity can be increased via transformation of the acetate group into an alcohol. If the hydrophilicity of the polymer is increased too far, however, and too much alcohol is introduced, the polymer itself becomes soluble in blood and thus does not effectively function as an embolic material. Conversely, if the hydrophobicity of the polymer is not decreased, the polymer is not sufficiently soluble in solvents which are both miscible in blood and safe for use in the human body.

The theoretical best solvent for our system is water because of its safety. Minimizing the amount of any solvent other than water is desirable. Solvents such as ethanol that are acceptable from a safety point of view do have independent and undesirable side effects when used in too high a concentration. Thus careful control of the hydrolysis ratio is desirable. Hydrolysis of about 15–30% of the acetate groups appears to be most effective. Said another way, the ratio of acetate groups to hydrolyzed acetate (alcoholic) sites is in the range of 2.0 to 6.0 and preferably is between 2.3 and 5.6.

Hydrolysis of PVAc takes place according to the following reaction:

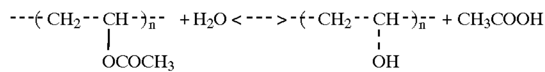

The reaction is reasonably fast and is an equilibrium reaction. The end point or degree of hydrolysis may be controlled by addition of specific amounts of the hydrolysis product—the acetic acid.

Since the composition is to be used in the human body, it is preferred to hydrolyze the PVAc feedstock in ethanol using an acidic catalyst such as HCl. Heat should be added to the reaction vessel only to the extent necessary to dissolve the PVAc. Excessive heat causes a side reaction (apparently an elimination reaction) resulting in a slightly orange tinge in the resulting partially hydrolyzed product.

In any event, the reaction may be carried out in the following way: PVAc is dissolved in an aqueous ethanolic solvent system, an appropriate amount of equilibrium-limiting acetic acid (the reaction product) is added, and the acidic catalyst is added. At 25° C., the reaction is typically complete in less than about two days.

The course of the reaction may be monitored using standard analytical techniques, e.g., titration using standardized NaOH solutions of the product solution (in acetone) with the remaining NaOH titrated to neutrality with a standardized HCl solution.

Once the desired level of hydrolysis is achieved, the partially hydrolyzed PVAC may be separated by precipitation in water. The precipitated product is typically then washed. The product may then be dried using vacuum (so to prevent heat degradation) and, in doing so, remove any remaining solvent.

Solvent Systems

Once the partially hydrolyzed PVAc has been dried and stripped of solvent, it is dissolved in a suitable solvent for use as an occludant precursor. Appropriate solvents are pharmaceutically acceptable in nature and are typically polar, substantially non-toxic and water miscible. Various suitable alcohols, ethers, amides, and glycols and their mixtures with each other or with water will be apparent to the worker of ordinary skill in this art. In general, the solvent or solvent system must be able to completely dissolve the partially hydrolyzed PVAc and upon introduction of that solution to a mammalian site containing an aqueous medium (naturally occurring or artificially introduced) allow the dissolved partially hydrolyzed PVAc to fall out of solution and form an agglomerate. Although many of these generically provided solvent systems would be suitable in certain situations where strong solvents would accelerate the occlusion activity of the partially hydrolyzed PVAc, e.g., where denaturing localized tissue would enhance the ultimate activity of causing tumor atrophy, an especially useful solvent system for the dissolution of partially hydrolyzed PVAc is a mixture of ethanol and water. Aqueous ethanolic solutions containing less than about 30% ethanol (by volume) do not dissolve the preferred partially hydrolyzed PVAc very well and solutions containing more than about 55% do not maintain most generally available non-ionic radio-opaque contrast media with efficiency. Consequently, the optimum solution for the preferred partially hydrolyzed PVAc polymers is an aqueous ethanolic solution containing between about 30% and 55% ethanol (by volume).

Embolic Agent Precursor

Because these inventive compositions are desirably used in regions of the vasculature which are both very tortuous and in which the vessel lumen are very narrow, the catheters through which these compositions are placed must be quite small. To allow ease of injection and to minimize the danger of immobilizing normal vessels around the desired treatment site, the viscosity of the inventive solution should be minimized, consistent with the other requirements noted herein.

Because the viscosity of a polymer solution is very sensitive to polymer molecular weight (MWw), particularly at high polymer concentration, the MWw of the polymer should be less than about 500,000. However, when the MW decreases, the polymer becomes increasingly soluble in water. Consequently, at lower MW, there is a chance that low molecular weight polymer would dissolve away from the precipitated polymer and act as a toxin. Therefore, it is desirable for the polymer to have a MW at least about than 10,000. The desired range is 10,000 to 500,000. The preferable MW is in the range of 50,000–100,000.

The concentration of polymer also affects both the viscosity of the solution as well as the precipitation behavior of the polymer. Principally because of the high viscosity of polymer solutions at high polymer concentration is quite unwieldy, partially hydrolyzed PVAc concentrations of less than 30% are preferred for immobilization. If the polymer concentration is lower, I have found that the polymer tends to fragment into small pieces when introduced into the bloodstream due to high stress from the blood flow. There is an increased chance for the precipitated polymer to pass the malformation site and to end up in the lungs. Therefore, I have found that about 7.5–30% polymer solutions are suitable for embolization. That is to say that "weight % polymer" is calculated based on the overall solution content (solvent, water, diluents, radio-opacifiers, etc.).

The partially hydrolyzed PVAc is soluble in an aqueous ethanolic solution containing far less ethanol than would be required for a similar PVAc polymer in the non-hydrolyzed condition. Aqueous ethanolic solutions of the partially hydrolyzed PVAc are able to dissolve higher loads of radio-opacifiers such as metrizamide (see, U.S. Pat. No. 3,701,771) or iopromide (see, U.S. Pat. No. 4,364,921). Iopromide is often sold in a dilute form under the tradename "Ultravist".

Methods of Use

Although the methods of using this inventive solution have been mentioned in passing above, additional description of preferred procedures may be found below. The inventive precursor is valuable in treating hepatic cancers and, in particular, for the treatment of hepatocellular carcinoma using portal vein embolization.

Generally speaking, the inventive precursor is introduced into the body in the following way. A catheter is introduced via usual procedures to a chosen site in a mammalian body. The site may be, e.g., a Fallopian tube, a ureteral or bile duct, a vascular site, etc. There are known devices for accessing each such site. Because of the viscosity of the solution, it is generally desirable to utilize the largest ID catheter practical in approaching the chosen site. The bolus of precursor material is then introduced into the catheter and injected into the chosen site. Because the polymer becomes nonsoluble and forms the occluding mass via the step of diluting its surroundings with an aqueous material, e.g., blood, the precursor should be introduced slowly so to form an aggregate near the catheter distal tip. More than one injection of precursor is possible using this technique. Once the mass is formed, the catheter is removed.

This procedure is especially useful in the treatment of various liver maladies, in particular for the treatment of cancers such as hepatocellular carcinoma via the occlusion of the feeding vessels to the region of the liver containing the cancer. The blood supply to the liver is from two major sources: about 30% is supplied from the hepatic artery (oxygen supply) and the remainder is supplied by the Portal vein coming from the intestines. The portal vein provides most of the nutrients needed by the liver. The liver is highly vascularized distal of the portal vein and is consequently an excellent site for use of the inventive precursor. Access to the portal vein is typically via direct puncture. Through that puncture site, various areas or segments of the liver may be easily accessed via use of catheters and fluoroscopy. Choice of occlusion site in the liver is dependent upon the site of the cancerous tissue and the vein feeding it. Occlusion using the procedure listed above is then used to close the chosen vessel. Surgical resection of the liver after occlusion and atrophy is then an option.

Barrier Solvents

When a blood vessel is catheterized, blood often refluxes into the distal end of catheter. Since the polymer of our inventive composition precipitates as the solvent mixes with blood, a polymer solution injected through a catheter could precipitate in the catheter. In such an event, the inventive polymer solution likely would not reach the treatment site. Thus, it is highly desirable to separate the inventive polymer solution from the blood during the period of its delivery through the catheter. A plug of a "barrier solvent" is suitable for such separation. Ideally, the barrier solvent is miscible neither with blood nor with the polymer solution. However, many such immiscible solvents would be expected to be toxic to the body. Consequently, an alternative is to use a less effective but nonetheless suitable solvent system, e.g., a partially miscible solvent system, to separate the polymer solution from the blood. A 20–30% aqueous ethanol solution is effective as a barrier.

EXAMPLES

The following examples are indicative of the invention but should not be considered as limiting the scope of the claimed invention in any way.

Example 1

Fourteen grams of the 15% hydrolyzed PVAc was dissolved in 55.4 grams of Ultravist 370 (UV 370), 33.75 grams of ethanol, and 17 grams of distilled water. The mass ratio of UV 370: ethanol:water was 52.2:31.8:16, and the volume ratio was 40:43:17. This composition has a radio-opacity equivalent to an iodine concentration of about 132 mg I/ml solution. To demonstrate the suitability of the precursor in occluding human AVM's, the solution was injected under fluoroscopic guidance to the rete mirabile of a pig. The vessels into and out of the rete were patent. The rete mirabile of a pig is similar in structure to a human AVM. The polymer precipitated inside the rete mirabile to completely obstruct the blood flow.

Example 2

Twelve grams of 20% hydrolyzed PVAc was dissolved in 55.4 grams of Ultravist 370, 32.6 grams of ethanol, 18.5 grams of distilled water. The mass ratio of UV 370: ethanol:water was 52.0:30.6:17.4, and the volume ratio was 40:41.5: 18.5. This composition was injected into a pig rete and successfully embolized the pig rete vessels. The material filled vessels smaller than did the Example 1 15% hydrolyzed PVAc precursor. Because of its high radio-opacity, the precipitated embolic material was visible under fluoroscopy even without the help of Digital Subtraction Angiography (DSA).

Example 3

Both 20% and 30% hydrolyzed PVAc were dissolved in equivalent mixtures of 78.95 grams of Ultravist 370 and 33.76 grams of ethanol. The mass ratio in each case was 70:30 and the volume ratio was 57:43. These solutions were used to embolize the portal vein in the right segment of pig livers. In each instance, the right segment of the liver shrank post-operatively (atrophy), while the left segment grew larger (hypertrophy). The PVAc with 20% hydrolysis was found to embolize arterioles as small as 100 $\mu$m, and 30% hydrolyzed PVAc up to 50 $\mu$m.

The embolization procedure was more convenient than that with gelform or fibrin glue, and the embolization was more complete and permanent. This example demonstrates that this compositions can be used to obliterate a part of an organ, especially with a tumor, to protect the organ and the body from cancer growth without the sacrifice of the whole organ.

Example 4

Twelve grams of 22% hydrolyzed PVAc was dissolved in 55.4 grams of Ultravist 370, 32.6 grams of ethanol, 18.5 grams of distilled water. The mass ratio of UV 370: ethanol:water was 52.0:30.6:17.4, and the volume ratio was 40:41.5: 18.5. This composition was injected into a pig rete and it successfully embolized the pig rete vessels. As was the case with the Example 2 materials, this material filled vessels smaller than did the Example 1 15% hydrolyzed PVAc. The embolic material was visible under fluoroscopy without the aid of Digital Subtraction Angiography (DSA).

Example 5

Polymers of 28% hydrolyzed PVAc and of 32% hydrolyzed PVAc were dissolved in equivalent mixtures of 78.95 grams of Ultravist 370 and 33.76 grams of ethanol. The mass ratio was 70:30 and the volume ratio was 57:43. When used for embolization of pig rete mirabile, the materials passed through the network of rete vessels and into cerebral arteries because the occlusion was too slow. The pig expired.

This example shows that highly hydrolyzed PVAc polymers when used in a human being may precipitate too slowly to form an acceptable polymeric aggregate and thus potentially pass an AVM and lodge in the lung. Consequently, the hydrolysis ratio should not be larger than about 25% for embolization of AVM's.

Example 6

22% and 28% hydrolyzed PVAc polymers were each dissolved in a mixture of solvents as described in Example 3. These solutions were used to embolize the kidney and portal veins of pig liver in the right segment. The embolized kidney shrank as time passed and in two months, the kidney collapsed completely. The embolized right segment of the liver shrank post-operatively (atrophy), while the left segment grew bigger (hypertrophy). The PVAc with 22% hydrolysis was found to embolize arterioles as small as 100 $\mu$m, and 28% hydrolyzed PVAc embolized arterioles of sizes up to 50 $\mu$m.

Example 7

A 40% hydrolyzed PVAc polymer was dissolved in a mixture of solvents as described in Example 3, and injected into pig kidney and portal veins for embolization. The precipitated material was difficult to see under fluoroscopy. The disadvantage with this precursor material is that the PVAc polymer does not bind the X-ray contrast material strongly; the contrast material did not remain with the precipitate. The low visibility of this composition could result in reflux of the embolic material and embolization of normal vessels. Thus PVAc with a hydrolysis ratio larger than 35% is not useful as an embolic material.

Example 8

In vitro studies using a number of polymer concentrations and hydrolysis ratios were conducted by adding a those solutions to a magnetically stirred circulating water bath. The embolic solutions were introduced into the circulating water through a needle. When the solution contained too low a polymer concentration, the polymer solution dispersed into small fragments instead of an aggregate. Small fragments are not good for AVM embolization. Solutions containing higher hydrolysis levels of hydrolyzed PVAc tend to disperse more. The polymer concentration should be larger than 5% for AVM embolization to prevent small fragments passing the AVM network into the draining vein. In the case of organ embolization, for example portal vein embolization, the embolic solution with low polymer concentration requires a large dose of embolic solution, which can be potentially harmful because of toxicity of solvent. Thus, polymer concentration larger than 5% is useful also for organ embolization.

Example 9

PVAc polymers with an average MW of 10,000 was hydrolyzed and used in the in vitro experiment described in Example 8, the polymer solution precipitated into small fragments instead of into an aggregate. Polymer solutions containing PVAc with an average MW smaller than 10,000 were not believed to be useful for AVM embolization. It is also true for organ embolization, because small fragments does not hold the X-ray contrast material strongly.

Example 10

PVAc polymers with an average MW of 300,000 were hydrolyzed and used in the in vitro experiment as described in Example 8. The polymer solution was too viscous to inject through a 3 French diameter. This experiment suggests that a polymer solution with an MW smaller than 300,000 is useful for embolization.

Example 11

A PVAc solution (30 wt % and MW of 50,000) was tested for injectability through a catheter as described in Example 10. The polymer solution was difficult to inject through a 3 French catheter. The polymer concentration should be less than 30wt%.

Example 12

The polymer solutions were also tested for miscibility with water-soluble X-ray contrast media. Non-ionic X-ray contrast materials were more soluble in ethanol-water mixtures than were ionic contrast media. Non-ionic contrast media solubility decreased with increase in ethanol concentration. The X-ray contrast media concentration was lower than 100 mg I/ml equivalent when the ethanol concentration is larger than 56% by volume. The embolic solutions with equivalent iodine concentrations lower than 100 mg I/ml are not useful in most clinical situations because of low visibility through fluoroscopy. Therefore the ethanol concentration for embolic solutions of hydrolyzed PVAc should be in the range of 30–55% by volume. When the ethanol concentration is lower than 30% by volume, the hydrolyzed PVAc useful for embolization is insoluble.

It is apparent that various modifications and changes may be made to the composition described above and to its method of use without departing from the spirit and scope of the invention as claimed below.

I claim as my invention:

1. An occludant precursor composition for forming an occlusion mass upon introduction of the precursor into a mammalian body comprising a solution of:

a.) partially hydrolyzed polyvinylacetate, b.) a pharmaceutically acceptable solvent, and c.) a soluble radio-opaque material.

2. The occludant precursor composition of claim 1 wherein the partially hydrolyzed polyvinylacetate has a molecular weight in the range of 10,000 to 500,000.

3. The occludant precursor composition of claim 1 wherein the partially hydrolyzed polyvinylacetate has a molecular weight in the range of 50,000 to 100,000.

4. The occludant precursor composition of claim 1 wherein the partially hydrolyzed polyvinylacetate has a ratio of acetate groups to hydrolyzed acetate sites in the range of 2.0 to 6.0.

5. The occludant precursor composition of claim 1 wherein the partially hydrolyzed polyvinylacetate has a ratio of acetate groups to hydrolyzed acetate sites in the range of 2.3 to 5.6.

6. The occludant precursor composition of claim 5 wherein the composition contains between 7.5 and 30% (wt) of partially hydrolyzed polyvinylacetate.

7. The occludant precursor composition of claim 1 wherein the pharmaceutically acceptable solvent comprises ethanol.

8. The occludant precursor composition of claim 1 wherein the pharmaceutically acceptable solvent comprises an aqueous ethanolic solution.

9. The occludant precursor composition of claim 1 wherein the pharmaceutically acceptable solvent comprises an aqueous ethanolic solution containing 30 to 55% (vol) ethanol.

10. The occludant precursor composition of claim 1 wherein the radio-opaque material comprises a material selected from the group consisting of iopromide, metrizamide, and mixtures and solutions thereof.

11. The occludant precursor composition of claim 10 wherein the radio-opaque material comprises iopromide.

12. The occludant precursor composition of claim 10 wherein the radio-opaque material comprises metrizamide.

13. A method for occluding a selected site in a mammalian body comprising the steps of:

a.) introducing to said selected site an occludant precursor composition for forming an occlusion mass, said precursor comprising a solution of:

i) partially hydrolyzed polyvinylacetate, and ii.) a pharmaceutically acceptable solvent, iii.) a soluble radio-opaque material, and b.) releasing said occludant precursor composition at said selected site to form said occlusion mass.

14. The method of claim 13 wherein the introducing step is carried out using a tubular member.

15. The method of claim 13 wherein the partially hydrolyzed polyvinylacetate has a molecular weight in the range of 10,000 to 500,000.

16. The method of claim 13 wherein the partially hydrolyzed polyvinylacetate has a molecular weight in the range of 50,000 to 100,000.

17. The method of claim 13 wherein the partially hydrolyzed polyvinylacetate has a ratio of acetate groups to hydrolyzed acetate sites in the range of 2.0 to 6.0.

18. The method of claim 13 wherein the partially hydrolyzed polyvinylacetate has a ratio of acetate groups to hydrolyzed acetate sites in the range of 2.3 to 5.6.

19. The method of claim 13 wherein the composition contains between 7.5 and 30% (wt) of partially hydrolyzed polyvinylacetate.

20. The method of claim 13 wherein the pharmaceutically acceptable solvent comprises ethanol.

21. The method of claim 13 wherein the pharmaceutically acceptable solvent comprises an aqueous ethanolic solution.

22. The method of claim 13 wherein the pharmaceutically acceptable solvent comprises an aqueous ethanolic solution containing 30 to 55% (vol) ethanol.

23. The method of claim 13 wherein the radio-opaque material comprises a material selected from the group consisting of iopromide, metrizamide, and mixtures and solutions thereof.

24. The method of claim 13 wherein the radio-opaque material comprises iopromide.

25. The method of claim 13 wherein the radio-opaque material comprises metrizamide.

26. The method of claim 14 wherein the tubular member is passed into the portal vein proximal of the liver.

27. An occludant precursor composition for forming an occlusion mass upon introduction of the precursor into a mammalian body comprising a solution of:

a.) partially hydrolyzed polyvinylacetate, and b.) a pharmaceutically acceptable solvent comprising an aqueous ethanolic solution containing 30 to 55% (vol) ethanol.

28. The occludant precursor composition of claim 27 wherein the partially hydrolyzed polyvinylacetate has a molecular weight in the range of 10,000 to 500,000.

29. The occludant precursor composition of claim 27 wherein the partially hydrolyzed polyvinylacetate has a molecular weight in the range of 50,000 to 100,000.

30. The occludant precursor composition of claim 27 wherein the partially hydrolyzed polyvinylacetate has a ratio of acetate groups to hydrolyzed acetate sites in the range of 2.0 to 6.0.

31. The occludant precursor composition of claim 27 wherein the partially hydrolyzed polyvinylacetate has a ratio of acetate groups to hydrolyzed acetate sites in the range of 2.3 to 5.6.

32. The occludant precursor composition of claim 31 wherein the composition contains between 7.5 and 30% (wt) of partially hydrolyzed polyvinylacetate.

33. The occludant precursor composition of claim 27 further comprising a radio-opaque material.

34. The occludant precursor composition of claim 33 wherein the radio-opaque material comprises a material selected from the group consisting of iopromide, metrizamide, and mixtures and solutions thereof.

35. The occludant precursor composition of claim 33 wherein the radio-opaque material comprises iopromide.

36. The occludant precursor composition of claim 33 wherein the radio-opaque material comprises metrizamide.

37. A method for occluding a selected site in a mammalian body comprising the steps of:

a.) introducing to said selected site an occludant precursor composition for forming an occlusion mass, said precursor comprising a solution of:

i) partially hydrolyzed polyvinylacetate, and ii.) a pharmaceutically acceptable solvent comprising an aqueous ethanolic solution containing 30 to 55% (vol) ethanol, and b.) releasing said occludant precursor composition to form said occlusion mass.

38. The method of claim 37 wherein the introducing step is carried out using a tubular member.

39. The method of claim 37 wherein the partially hydrolyzed polyvinylacetate has a molecular weight in the range of 10,000 to 500,000.

40. The method of claim 37 wherein the partially hydrolyzed polyvinylacetate has a molecular weight in the range of 50,000 to 100,000.

41. The method of claim 37 wherein the partially hydrolyzed polyvinylacetate has a ratio of acetate groups to hydrolyzed acetate sites in the range of 2.0 to 6.0.

42. The method of claim 37 wherein the partially hydrolyzed polyvinylacetate has a ratio of acetate groups to hydrolyzed acetate sites in the range of 2.3 to 5.6.

43. The method of claim 37 wherein the composition contains between 7.5 and 30% (wt) of partially hydrolyzed polyvinylacetate.

44. The method of claim 37 wherein the composition further comprises a radio-opaque material.

45. The method of claim 44 wherein the radio-opaque material comprises a material selected from the group consisting of iopromide, metrizamide, and mixtures and solutions thereof.

46. The method of claim 44 wherein the radio-opaque material comprises iopromide.

47. The method of claim 44 wherein the radio-opaque material comprises metrizamide.

48. The method of claim 37 wherein the tubular member is passed into the portal vein proximal of the liver.

* * * * *